(12) United States Patent
Bogdan et al.

(10) Patent No.: US 7,297,830 B2
(45) Date of Patent: Nov. 20, 2007

(54) PROCESS FOR ISOMERIZING NON-EQUILIBRIUM XYLENE-CONTAINING FEED STREAMS

(75) Inventors: Paula L. Bogdan, Mount Prospect, IL (US); James E. Rekoske, Glenview, IL (US); Robert B. Larson, Chicago, IL (US); Patrick C. Whitchurch, Villa Park, IL (US); John E. Bauer, LaGrange Park, IL (US); Michael H. Quick, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 240 days.

(21) Appl. No.: 11/226,493

(22) Filed: Sep. 14, 2005

(65) Prior Publication Data

US 2007/0060778 A1 Mar. 15, 2007

(51) Int. Cl.
*C07C 5/22* (2006.01)
(52) U.S. Cl. .................. 585/481; 585/482; 585/480
(58) Field of Classification Search .............. 585/481, 585/482, 480
See application file for complete search history.

(56) References Cited

U.S. PATENT DOCUMENTS

| | | | |
|---|---|---|---|
| 3,201,491 A | 8/1965 | Stine et al. ............. 260/676 |
| 3,626,020 A | 12/1971 | Neuzil ................. 260/674 SA |
| 3,696,107 A | 10/1972 | Neuzil ................. 260/674 SA |
| 4,039,599 A | 8/1977 | Gewartowski .......... 260/668 A |
| 4,184,943 A | 1/1980 | Anderson .............. 208/310 R |
| 4,310,440 A | 1/1982 | Wilson et al. ............. 252/435 |
| 4,362,653 A | 12/1982 | Robinson ............... 252/455 R |
| 4,381,419 A | 4/1983 | Wylie ........................ 585/828 |
| 4,402,832 A | 9/1983 | Gerhold .................... 210/659 |
| 4,435,608 A * | 3/1984 | Koetsier et al. ........... 585/480 |
| 4,440,871 A | 4/1984 | Lok et al. .................. 502/214 |
| 4,793,984 A | 12/1988 | Lok et al. .................. 423/306 |
| 4,899,011 A | 2/1990 | Chu et al. .................. 585/481 |
| 4,899,012 A | 2/1990 | Sachtler et al. ........... 585/482 |
| 6,090,289 A | 7/2000 | Verduijn et al. .......... 210/644 |
| 6,143,941 A | 11/2000 | Sharma et al. ............ 585/481 |
| 6,280,608 B1 | 8/2001 | Jensen et al. .............. 208/143 |
| 6,573,418 B2 | 6/2003 | Miller et al. .............. 585/826 |
| 6,710,003 B2 | 3/2004 | Jan et al. .................... 502/60 |

\* cited by examiner

*Primary Examiner*—Thuan Dinh Dang
(74) *Attorney, Agent, or Firm*—Maryann Maas

(57) ABSTRACT

Reduced co-production of toluene and $C_9$ and higher aromatics such as trimethylbenzene, methylethylbenzene, and diethylbenzene is achieved in processes for the isomerization of xylenes to close to equilibrium using a layered catalyst having a thin outer layer of molecular sieve and hydrogenation metal component on a core, wherein at least about 75 mass-% of the hydrogenation metal component is in the outer layer.

20 Claims, No Drawings

PROCESS FOR ISOMERIZING NON-EQUILIBRIUM XYLENE-CONTAINING FEED STREAMS

FIELD OF THE INVENTION

This invention relates to catalytic processes for the isomerization of xylenes with desirably low $C_8$ aromatic ring loss as observed by co-production of toluene and trimethylbenzene.

BACKGROUND OF THE INVENTION

Numerous processes have been proposed for the isomerization of one or more of xylenes (meta-xylene, ortho-xylene and para-xylene) to form other isomers of xylene. In many instances, the sought xylene isomer is para-xylene due to the demand for terephthalic acid for the manufacture of polyester.

In general, these xylene isomerization processes comprise contacting the xylene isomer sought to be isomerized with an isomerization catalyst under isomerization conditions. Various catalysts have been proposed for xylene isomerization. These catalysts include molecular sieves, especially molecular sieves contained in a refractory, inorganic oxide matrix. The catalysts also contain a hydrogenation metal, such as a platinum group metal.

Due to the large scale of commercial facilities to produce para-xylene on an economically competitive basis, not only must a xylene isomerization process be active and stable, but it also must not unduly convert xylenes to other aromatics or crack the aromatic feed so as to result in ring loss. Toluene and trimethylbenzene are two of the typical co-products from an isomerization and, because a loss in $C_8$ aromatic values results from such co-production, processes to reduce their co-production are sought. Typically, the loss in $C_8$ aromatic values increases as the isomerization process is driven closer to equilibrium. Accordingly, to minimize the loss of $C_8$ aromatic values, commercial facilities often suffer inefficiencies by not driving the isomerization close to equilibrium.

Catalytic processes are sought that reduce the loss of $C_8$ aromatic values and thus reduce the co-production of toluene and trimethylbenzene and other $C_9$ and higher aromatics while allowing closer approaches to xylene isomerization equilibrium to be achieved.

U.S. Pat. No. 4,362,653, for instance, discloses a hydrocarbon conversion catalyst which could be used in the isomerization of isomerizable alkylaromatics that comprises silicalite (having an MFI-type structure) and a silica polymorph. The catalyst may contain optional ingredients. Molybdenum is listed as one of the many optional ingredients. U.S. Pat. No. 4,899,012 discloses catalyst for isomerization and conversion of ethylbenzene containing a Group VIII metal, lead, a pentasil zeolite and an inorganic oxide binder. U.S. Pat. No. 6,573,418 discloses a pressure swing adsorption process to separate para-xylene and ethylbenzene from $C_8$ aromatics. Included among the catalysts disclosed for ethylbenzene isomerization are those containing ZSM-5 type of molecular sieve (Al-MFI) dispersed on silica. The catalysts contain a hydrogenation metal and listed among the hydrogenation metals are molybdenum. Suitable matrix materials are said to be alumina and silica. See example 12 which uses a molybdenum-containing catalyst for xylene isomerization. U.S. Pat. No. 6,143,941 discloses selective isomerization and ethylbenzene conversion processes using catalysts comprising a zeolite, including MFI-type zeolites, a platinum group metal and an aluminophosphate binder.

U.S. Pat. No. 4,899,011 discloses a two catalyst system for xylene isomerization and ethylbenzene dealkylation in which the first catalyst, which has low ethylbenzene diffusivity, dealkylates ethylbenzene, and the second catalyst, which has a greater ethylbenzene diffusivity, effects xylene isomerization.

U.S. Pat. No. 6,280,608 discloses layered catalysts containing a core and an outer layer containing molecular sieve and catalytic metals. One of the potential uses for the layered catalyst is said to be for isomerization reactions.

SUMMARY OF THE INVENTION

In accordance with this invention processes for the isomerization of xylenes are provided that exhibit reduced $C_8$ ring loss by the co-production of toluene and $C_9$ and higher aromatics such as trimethylbenzene, methylethylbenzene, and diethylbenzene while achieving a xylene isomerization close to equilibrium. These processes use a catalyst having a core, or support, upon which a thin layer of molecular sieve and hydrogenation metal component is placed. This thin layer uses a binder preferably containing aluminum phosphate. The catalysts used in the processes of this invention have at least about 75, preferably at least about 90, mass-% of the hydrogenation metal in the thin layer. Not only do the composite catalysts used in this invention provide the sought reduced co-production of toluene and $C_9$ and higher aromatics even at close approaches to xylene equilibrium, but also, if desired, the amount of molecular sieve and hydrogenation metal per unit volume of reactor can be reduced. Moreover, the composite catalyst can have shapes such as rings, saddles, and honeycombs, which shapes are not as readily achievable with a homogeneous catalyst composition.

The broad aspects of the processes of this invention for isomerizing xylene in a feed stream comprising a non-equilibrium mixture of one or more xylenes comprise contacting the feed stream with a catalytically-effective amount of layered catalyst under isomerization conditions sufficient to provide a xylene-containing isomerization product stream in which of the xylenes, para-xylene comprises at least about 23 mass-%, ortho-xylene at least about 21 mass-%, and meta-xylene at least about 48 mass-%, said catalyst comprising a shape-defining core, preferably having a major dimension of at least about 300 microns, a layer on said core. The core is shape-defining, i.e., the core, and not the layer, defines the geometric configuration of the catalyst. The layer is typically the outer layer of the catalyst; however, it is within the scope of this invention that an additional layer may be placed on the catalyst that does not adversely affect the catalytic performance of the layer. For sake of ease of reference herein, the layer will be referred to herein as the outer layer.

The outer layer comprises molecular sieve having a pore diameter of from about 4 to 8 angstroms, at least one hydrogenation metal component and a binder. The outer layer has a thickness less than about 250, preferably between about 20 and 200, and more preferably between about 20 and 150, microns. The at least one hydrogenation metal component is selected from metals of Groups 6 to 10 of the Periodic Table (IUPAC), wherein at least about 75 mass-% of the hydrogenation metal component in the catalyst is contained in the layer. In the processes of this invention, the net production of toluene and trimethylbenzene is less than about 3, preferably less than about 2.5, and most preferably less than about 2, mass-% of the total xylenes and ethylbenzene, if present, in the feed stream.

Preferably, the processes are used in the production of para-xylene and the feed stream contains less than about 5 mass-% para-xylene based on total xylenes. Under conditions where ethylbenzene is dealkylated or the feed contains little or no ethylbenzene, the approach to equilibrium can often be such that the isomerization product contains at least about 23.5, and more preferably at least about 23.7, mass-% para-xylene based on total xylenes.

In a further preferred aspect of the processes of the invention, the feed stream contains ethylbenzene, e.g., from about 1 to 60 mass-% based upon total $C_8$ aromatics, and the ethylbenzene is dealkylated.

In a further preferred aspect of the processes of this invention wherein the feed stream comprises ethylbenzene and a non-equilibrium mixture of xylenes, the ethylbenzene is either isomerized or dealkylated. The isomerization or dealkylation may be effected using the layered catalyst. In an alternate aspect of the processes of this invention, the feed stream is contacted with a catalyst suitable for ethylbenzene dealkylation under ethylbenzene dealkylation conditions to provide a dealkylation product stream which is then contacted with the layered catalyst for effecting isomerization of xylenes. Preferably, for ethylbenzene dealkylation, the feed stream contains less than about 0.5 mass-% naphthenes.

DETAILED DISCUSSION

Catalyst

The processes of this invention use a layered catalyst composition. The layered catalyst composition comprises an inner core and an outer layer containing molecular sieve and hydrogenation metal component. The composite catalyst may be of any suitable structure and configuration and made by any suitable process. For instance, see U.S. Pat. Nos. 6,280,608 and 6,710,003 disclose layered catalyst compositions and their preparation and are hereby incorporated in their entireties by reference.

The core may be of any suitable material capable of providing the structure and tolerating the process conditions. The core may be homogeneous or may itself be a composite. The preferred composition of the core is one that does not have significant adverse effect in the isomerization process. Thus, the core would have a substantially lower catalytic activity for isomerization relative to the outer layer. The inner core may be essentially inert in the process environment. The characteristics of the inner core should also be properly matched with those of the outer layer, such that a strong, attrition resistant bond is formed during the composition preparation steps outlined hereinafter.

Examples of the inner core materials include, but are not limited to, refractory inorganic oxides, silicon carbide, and metals. Examples of refractory inorganic oxides include without limitation cordierite, alpha alumina, theta alumina, magnesia, zirconia, titania and mixtures thereof. A preferred inorganic oxide is alpha alumina. Other core materials include clays such as montmorillonite, saponite, kaolinite, and bentonite. The core may be composed of metals and ceramic-coated metals. Advantageously, the material of the core and that of the layer have similar coefficients of expansion over the temperature ranges to which the composites are exposed during preparation and use.

The materials that form the inner core can be formed into a variety of shapes such as pellets, extrudates, spheres, rings, trilobes, saddles, or other physical forms including monoliths such as honeycomb structures, plates, tubes, and the like. Of course, not all materials can be formed into each shape. The core typically has a major dimension, usually at least about 300 microns, which is in excess of the thickness of the outer layer and thus significantly defines the shape of the composite catalyst.

One broad grouping of preparation techniques to make the inner core include oil dropping, pressure molding, metal forming, pelletizing, granulation, extrusion, rolling methods and marumerizing. A spherical inner core is commonly used, although pressure drop considerations can warrant the use of shaped articles that result in a higher void fraction when such shapes are packed into a catalyst bed. The inner core whether spherical or not has an effective diameter of about 0.05 mm to about 5 mm and preferably from about 0.4 mm to about 3 mm. For a non-spherical inner core, effective diameter is defined as the diameter the shaped article would have if it were molded into a sphere. Once the inner core is prepared, it is calcined at a temperature of about 400° to about 1500° C.

The outer layer contains molecular sieve and binder. Molecular sieves include those having $Si:Al_2$ ratios greater than about 10, and often greater than about 20, such as the MFI, MEL, EUO, FER, MFS, MTT, MTW, TON, MOR, UZM-8 and FAU types of zeolites. Pentasil zeolites such as MFI, MEL, MTW and TON are preferred, and MFI-type zeolites, such as ZSM-5, silicalite, Borolite C, TS-1, TSZ, ZSM-12, SSZ-25, PSH-3, and ITQ-1 are especially preferred where ethylbenzene is dealkylated. MTW-type molecular sieves are especially preferred for processes in which ethylbenzene is isomerized.

The relative proportion of molecular sieve in the outer layer may range from about 1 to about 99 mass-%, with about 2 to about 90 mass-% being preferred. A refractory binder or matrix is typically used to facilitate fabrication of the isomerization catalyst, provide strength and reduce fabrication costs.

The binder should be uniform in composition and relatively refractory to the conditions used in the process. Suitable binders include inorganic oxides such as one or more of alumina, aluminum phosphate, magnesia, zirconia, chromia, titania, boria and silica. The catalyst also may contain, without so limiting the composite, one or more of (1) other inorganic oxides including, but not limited to, beryllia, germania, vanadia, tin oxide, zinc oxide, iron oxide and cobalt oxide; (2) non-zeolitic molecular sieves, such as the aluminophosphates of U.S. Pat. No. 4,310,440, the silicoaluminophosphates of U.S. Pat. No. 4,440,871 and ELAPSOs of U.S. Pat. No. 4,793,984; and (3) spinels such as $MgAl_2O_4$, $FeAl_2O_4$, $ZnAl_2O_4$, $CaAl_2O_4$, and other like compounds having the formula $MO—Al_2O_3$ where M is a metal having a valence of 2; which components can be added to the composite at any suitable point.

A preferred binder or matrix component, especially for processes also involving the dealkylation of ethylbenzene, comprises an amorphous phosphorous-containing alumina (hereinafter referred to as aluminum phosphate) component. The atomic ratios of aluminum to phosphorus in the aluminum phosphate binder/matrix generally range from about 1:10 to 100:1, and more typically from about 1:5 to 20:1. Preferably, the aluminum phosphate has a surface area of up to about 450 $m^2/g$, and preferably the surface area is up to about 250 $m^2/g$. See, for instance, U.S. Pat. No. 6,143,941.

The thickness of the outer layer is less than about 250 microns and preferably is less than 200 microns, for instance, 20 to 200, microns. Often the thickness is within the range of about 20 to 100 microns. Preferably, the thickness is such that a combination of adequate catalytic activity for the isomerization with low activity for transalkylation, which transalkylation results in $C_8$ ring loss, is achieved. Without wishing to be limited to theory, it is believe that the close approaches to xylene isomerization equilibrium with little co-production of toluene and $C_9$ and higher aromatics of the processes of this invention are, in part, enabled by the use of a thin outer layer that facilitates diffusion of the aromatics to and from catalytically active sites, and the presence of catalytically active sites for the isomerization located close to the surface of the catalyst composite. Accordingly, the outer layer should be sufficiently thin that the net production of toluene and trimethylbenzene is less than about 3, preferably less than about 2.5, and most preferably less than about 2, mass-% of the total xylenes and ethylbenzene (if present) in the feed stream. And by having the catalytically active sites for the isomerization clustered in this thin, outer layer, the sought catalytic isomerization activity for xylene isomerization can be achieved.

The outer layer can be applied to the core in any suitable manner. If desired, a bonding layer may be used to assist in adhering the outer layer to the core. In many instances, the coating can be directly applied to the core. The outer layer comprises molecular sieve and binder. It is often possible to synthesize molecular sieve, e.g., MFI, in situ as a layer on the core by various techniques. See, for instance, U.S. Pat. No. 6,090,289 and references cited therein for techniques to make molecular sieve films on supports. In such processes, the binder may be coated on the core prior to or after the in situ synthesis of the molecular sieve.

Alternatively, the molecular sieve and the binder slurry may be preformed and coated on the core. The binder may be in the form of a sol, hydrosol or acidic sol, or the like. The amount of the sol contained in the slurry is based upon the desired ratio of binder to molecular sieve. If desired, the slurry may contain one or more bonding agents to aid in adhesion to the core and improve the strength of the outer layer. Examples of bonding agents include but are not limited to polyvinyl alcohol (PVA), hydroxy propyl cellulose, methyl cellulose, and carboxy methyl cellulose. The amount of organic bonding agent which is added to the slurry will vary considerably from about 0.1 to about 5 mass-% of the slurry. Depending on the particle size of the outer layer, it may be necessary to mill the slurry in order to reduce the particle size and simultaneously give a narrower particle size distribution. This can be done by means known in the art such as ball milling for times of about 30 minutes to about 5 hours and preferably from about 1.5 to about 3 hours. Often the slurry for coating the core has a sufficient liquid (usually water) content that the viscosity is in the range from about 30 to 600 centipoise (millipascal second) at 25° C.

Coating of the inner core with the slurry can be accomplished by means such as rolling, dipping, spraying, etc. to yield a coated core having an outer layer. One coating technique involves using a fixed fluidized bed of inner core particles and spraying the slurry into the bed to coat the particles evenly. The thickness of the layer of the coated core can vary considerably, but usually is from about 5 to about 250 microns, preferably from about 10 to about 200 microns, with the average coating thickness being between about 20 and 200 microns.

Once the inner core is coated with the outer bound zeolite layer, the resultant coated core is dried at a temperature of about 50° to about 300° C. for a time of about 1 to about 24 hours to provide a dried coated core. Subsequently, the dried coated core is calcined at a temperature of about 400° to about 900° C. for a time of about 0.5 to about 10 hours to effectively bond the outer layer to the inner core and provide the layered catalyst composition of the present invention. The calcination step also removes any remaining organic template material within the molecular sieve as well as any residual bonding agent. In some cases, the catalyst may be activated in a modified calcination step wherein the organic template is first decomposed in a flow of pure nitrogen. The oxygen concentration is then gradually increased to combust any residual hydrocarbons in the zeolite. It is also possible to combine the drying and calcining operations into a single step. If desired, the calcination can occur subsequent to impregnation of hydrogenation metal component.

If desired, the composite structure, before or after impregnation with the hydrogenation metal component, can be subjected to steaming to tailor its acid activity. The steaming may be effected at any stage, but usually is carried out on the composite prior to incorporation of the hydrogenation metal component. Steaming conditions comprise a water concentration of about 5 to 100 vol-%, pressure of from about 100 kPa to 2 MPa, and temperature of between about 600° and 1200° C.; the steaming temperature preferably between about 650° and 1000° C., more preferably at least about 750° C. and optionally may be about 775° C. or higher. In some cases, temperatures of about 800° to 850° C. or more may be employed. The steaming should be carried out for a period of at least one hour, and periods of 6 to 48 hours are preferred.

Alternatively or in addition to the steaming, the composite may be washed with one or more of a solution of ammonium nitrate, a mineral acid, and/or water. Considering the first alternative, the catalyst may be washed with a solution of about 5 to 30 mass-% ammonium nitrate. When acid washing is employed, a mineral acid such as HCl or $HNO_3$ is preferred; sufficient acid is added to maintain a pH of from more than 1 to about 6, preferably from about 1.5 to 4. The catalyst is maintained in a bed over which the solution and/or water is circulated for a period of from about 0.5 to 48 hours, and preferably from about 1 to 24 hours. The washing may be effected at any stage of the preparation, and two or more stages of washing may be employed.

Prior to addition of the hydrogenation metal component the composite preferably is ion-exchanged with a salt solution containing at least one hydrogen-forming cation such as $NH_4^+$ or quaternary ammonium. The hydrogen-forming cation replaces principally alkali-metal cations to provide, after calcination, the hydrogen form of the zeolite component.

One or more hydrogenation metal components are provided. Hydrogenation metal components are selected from the metals of Groups 6 to 10 of the Periodic Table (IUPAC), preferably molybdenum, rhenium and platinum-group metal. Preferred platinum-group metals include one or more of platinum, palladium, rhodium, ruthenium, osmium, and iridium. The most preferred platinum-group metals are platinum and palladium, with platinum being especially preferred.

The hydrogenation metal component is contained in the outer layer of the catalyst composite. The location of the hydrogenation metal component within the catalyst can often be determined by scanning electron microscopy. At least about 75, and preferably at least about 90, mass-% of the hydrogenation metal component is within the outer layer. As the outer layer contains the molecular sieve, a close association of molecular sieve to the hydrogenation metal is assured. While not wishing to be limited by theory, the close association of the hydrogenation metal with the molecular sieve is believed to aid in reducing transalkylation reactions leading to the generation of toluene and $C_9$ and higher aromatics.

Any suitable technique may be used to selectively provide the hydrogenation metal component in the outer layer. For instance, the hydrogenation metal component may not be attracted by the material of the core, the hydrogenation metal component may be composited with the material of the outer layer prior to making the layered catalyst composite, the binder may be selected such that the hydrogenation metal component is deposited therein as opposed to the material of the core, the surface of the core may be relatively impermeable to the hydrogenation metal component or precursor, or the hydrogenation metal component deposition technique may be such that the component becomes fixed in the outer layer prior to being able to pass to the core.

With respect to platinum group metals, the platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all of the platinum-group metal component exists in a reduced state. The platinum-group metal component generally comprises from about 10 to about 10,000 mass-ppm (parts per million) of the outer layer of the composite, calculated on an elemental basis, with a level of about 100 to about 2000 mass-ppm being particularly suitable. When using a platinum component, very low levels of about 100 to 500 mass-ppm of platinum based on the outer layer of the catalyst, on an elemental basis, are favored. When using a palladium component, levels of about 200 to 2000 mass-ppm of palladium based on the outer layer, on an elemental basis, are favored.

The platinum-group metal component may be incorporated into the catalyst composite in any suitable manner. One method of preparing the catalyst involves the utilization of a water-soluble, decomposable compound of a platinum-group metal to impregnate the outer layer. Alternatively, a platinum-group metal compound may be added at the time of compositing the outer layer. Yet another method of effecting a suitable metal distribution is by compositing the metal component with the binder prior to applying the coating to make the outer layer. Complexes of platinum-group metals which may be employed according to the above or other known methods include chloroplatinic acid, chloropalladic acid, ammonium chloroplatinate, bromoplatinic acid, platinum trichloride, platinum tetrachloride hydrate, platinum dichlorocarbonyl dichloride, tetraamineplatinum chloride, dinitrodiaminoplatinum, sodium tetranitroplatinate (II), palladium chloride, palladium nitrate, palladium sulfate, diaminepalladium (II) hydroxide, tetraaminepalladium (II) chloride, and the like.

Where the hydrogenation metal comprises molybdenum, molybdenum is usually present in an amount of 0.1 to 5 mass-% based upon the mass of the outer layer. One useful process for making the catalysts comprises forming the catalyst composite without the molybdenum component and then impregnating or otherwise depositing on the composite with a molybdenum compound such as ammonium heptamolybdate, molybdenum trioxide, ammonium dimolybdate, molybdenum oxychloride, molybdenum halides, e.g., molybdenum chloride and molybdenum bromide, molybdenum carbonyl, phosphomolybdates, and heteromolybdic acids. Usually water soluble molybdenum compounds are selected as the source of the molybdenum component for the catalyst. The molybdenum-containing catalysts may also contain at least one platinum group metal as a hydrogenation metal catalyst components. Usually, the molybdenum (calculated on an elemental basis) comprises at least about 60 atomic-percent, preferably at least about 80 atomic-percent to essentially all, of the hydrogenation metal (elemental basis) of the hydrogenation component. Often, the platinum group metal present is in an amount of 20 to 500 mass-ppm based on the mass of the outer layer.

After addition of the hydrogenation metal component, the resultant catalytic composite usually is dried at a temperature of about 100° to about 320° C. for a period of from about 1 to about 24 or more hours. The dried composite then is calcined at a temperature of from about 400° to about 600° C. in an air atmosphere for a period of from about 0.1 to 10 hours to convert the metallic components substantially to the oxide form.

The calcined composite optimally is subjected to a substantially water-free reduction step to ensure a uniform and finely divided dispersion of the optional metallic components. The reduction optionally may be effected on the catalyst as loaded in the isomerization-process reactor of the present invention prior to the startup of the isomerization process. Substantially pure and dry hydrogen (i.e., less than 20 vol-ppm $H_2O$) preferably is used as the reducing agent in this step. The reducing agent contacts the catalyst at conditions, including a temperature of from about 200° to about 650° C. and for a period of is from about 0.5 to about 10 hours, effective to reduce substantially all of the platinum group metal component to the metallic state. The catalysts of the may contain a halogen component, comprising fluorine, chlorine, bromine or iodine or mixtures thereof, with chlorine being preferred. Preferably, however, the catalyst contains no added halogen other than that associated with other catalyst components. In some cases the resulting reduced catalyst composite may also be beneficially subjected to presulfiding by a method known in the art to incorporate in the catalyst composite from about 0.01 to about 0.5 mass-% sulfur, calculated on an elemental basis, into the catalyst.

With respect to hydrogenation components from Groups 6 and 7, especially molybdenum-containing catalysts and rhenium-containing catalysts, the hydrogenation metal component generally comprises from about 0.1 to about 5 mass-% of the final catalyst calculated as hydrogenation component being the elemental metal based upon the mass of the outer layer. The hydrogenation metal component may exist within the final catalyst composite as a compound such as an oxide, sulfide, halide, oxysulfide, etc., or as an elemental metal or in combination with one or more other ingredients of the catalyst composite.

The hydrogenation metal component may be incorporated into the catalyst composite in any suitable manner. One method of preparing the catalyst involves the utilization of a water-soluble, decomposable compound of the hydrogenation metal to impregnate the calcined sieve/binder composite. Alternatively, a hydrogenation metal compound may be added at the time of compositing the sieve component and binder.

The catalyst composites are dried at a temperature of from about 100° to about 320° C. for a period of from about 2 to about 24 or more hours. If desired, the catalyst may be calcined at a temperature of from about 400° to about 650° C. in an air atmosphere for a period of from about 0.1 to about 10 hours. Steam may also be present during the calcination, e.g., from about 0.5 to 20, say, about 1 to 10, mol-% steam based on the air.

In some cases, the catalyst composite may also be beneficially subjected to presulfiding by a method known in the art to incorporate in the catalyst composite from about 0.05 to about 1.0 mass-% sulfur calculated on an elemental basis. Particularly advantageous catalysts are sulfided sufficiently to enhance activity, and this sulfiding may be through presulfiding, or adding a sulfur-containing sulfiding agent to the feedstream during use of the catalyst. Preferably, the elemental ratio of sulfur to molybdenum is between about 0.01:1 to 3:1, more preferably, about 0.1 to 2:1.

If desired, the catalyst may contain, as a minor portion of the hydrogenation catalyst component, a platinum-group metal, including one or more of platinum, palladium, rhodium, ruthenium osmium, and iridium. In any event, the Group 6 or 7 hydrogenation metal component comprises at least about 60 atomic-percent, preferably at least about 80 atomic-percent to essentially all, of the hydrogenation metal (elemental basis) of the hydrogenation component. Often, any platinum group metal present is in an amount of 20 to 500 mass-ppm based on the outer layer. Where the catalyst contains a minor amount, based on total hydrogenation metal, of platinum group metal, the resultant calcined composites often are subjected to a substantially water-free reduction step to ensure a uniform and finely divided dispersion of the optional metallic components. The reducing agent contacts the catalyst at conditions, including a temperature of from about 200° to about 650° C. and for a period of from about 0.5 to about 10 hours, effective to reduce substantially all of the platinum group metal component to the metallic state. It is within the scope of the present invention that the catalyst may contain other metal components known to modify the effect of the hydrogenation metal component. Such metal modifiers may include without so limiting the invention rhenium, tin, germanium, lead, cobalt, nickel, indium, gallium, zinc, and mixtures thereof. Catalytically effective amounts of such metal modifiers may be incorporated into the catalyst by any means known in the art to effect a homogeneous or stratified distribution.

Where a molybdenum-containing catalyst is used, sometimes sulfiding can enhance isomerization activity. Sulfiding conditions are those in which the sulfiding agent is incorporated into the catalyst without forming sulfur dioxide. The sulfiding may be done during the catalyst preparation or thereafter, including as a pretreatment at catalyst start-up or during use of the catalyst. The sulfiding may be conducted in any convenient manner. For instance, a solid or sorbed sulfur-containing component, i.e., sulfiding agent, may be incorporated into the catalyst composite which decomposes during the catalyst preparation or during start-up or use of the catalyst. Alternatively, the formed catalyst may be contacted with a liquid or gaseous sulfiding agent under sulfiding conditions. Examples of sulfiding agents include hydrogen sulfide, carbonyl sulfide, carbon disulfide, salts, especially ammonium and organo salts, of sulfates, bisulfates, sulfites, and bisulfites, sulfur dioxide, sulfur trioxide, organosulfides, e.g., dimethyl sulfide, diethyl sulfide, and methyl ethyl sulfide; mercaptans, e.g., methyl mercaptan, ethyl mercaptan, and t-butyl mercaptan; thiophenes, e.g., tetrahydrothiophene.

The sulfiding conditions can vary widely and will depend upon the nature to the sulfiding agent and the extent of sulfiding desired. For instance, with oxygen-containing sulfur compounds, the sulfiding conditions should be sufficient to reduce the sulfur moiety to sulfide. The selection of the sulfiding conditions will also be influenced limits of feasibility at the location of the catalyst undergoing sulfiding. Thus, different conditions may be preferred where the sulfiding is being conducted after the catalyst has been installed in a reactor for the isomerization as would be preferred where the catalyst is at a facility for the manufacture of catalyst. In general, the sulfiding may be conducted over a temperature range of 0° to 600° C., preferably about 10° to 500° C. and a pressure of from about 10 to 5000 or more kPa absolute. The duration of the sulfiding will depend upon the other conditions of the sulfiding, e.g., the sulfiding agent, the concentration of the sulfiding agent, and sulfiding temperature, as well as the amount of sulfur to be incorporated into the catalyst. Usually the sulfiding is conducted for a period of time of at least about 10 minutes, and may, in the case of in situ sulfiding in an isomerization reactor, be continuous. Where the sulfiding is accomplished during the preparation of the catalyst, the sulfiding is usually done over a period of at least about 10 minutes, e.g., 10 minutes to 24 hours. Often, the sulfiding is done in the presence of hydrogen, e.g., at a partial pressure of about 10 to 5 MPa.

Where sulfiding is done while the catalyst is in an isomerization reactor, the sulfiding may be accomplished as a pretreatment or during the isomerization process itself. In the latter case, the sulfiding agent is usually provided in a low concentration, e.g., less than about 50, say about 0.001 to 20, mass-ppm of the feedstock.

Catalysts may be regenerated. Where the loss of catalytic activity is due to coking of the catalyst, conventional regeneration processes such as high temperature oxidation of the carbonaceous material on the catalyst may be employed.

PROCESS

The feedstocks to the aromatics isomerization process of this invention comprise non-equilibrium xylene and ethylbenzene. These aromatic compounds are in a non-equilibrium mixture, i.e., at least one $C_8$ aromatic isomer is present in a concentration that differs substantially from the equilibrium concentration at isomerization conditions. Thus, a non-equilibrium xylene composition exists where one or two of the xylene isomers are in less than equilibrium proportion with respect to the other xylene isomer or isomers. The xylene in less than equilibrium proportion may be any of the para-, meta- and ortho-isomers. As the demand for para- and ortho-xylenes is greater than that for meta-xylene, usually, the feedstocks will contain meta-xylene. Generally, the mixture will have an ethylbenzene content of about 1 to about 60 mass-%, an ortho-xylene content of 0 to about 35 mass-%, a meta-xylene content of about 20 to about 95 mass-% and a para-xylene content of 0 to about 30 mass-%. Usually the non-equilibrium mixture is prepared by removal of para-, ortho- and/or meta-xylene from a fresh $C_8$ aromatic mixture obtained from an aromatics-production process. The feedstocks may contain other components, including, but not limited to naphthenes and acyclic paraffins, as well as higher and lower molecular weight aromatics.

The alkylaromatic hydrocarbons may be used in the present invention as found in appropriate fractions from various refinery petroleum streams, e.g., as individual components or as certain boiling-range fractions obtained by the selective fractionation and distillation of catalytically cracked or reformed hydrocarbons. Concentration of the isomerizable aromatic hydrocarbons is optional; the process of the present invention allows the isomerization of alkylaromatic-containing streams such as catalytic reformate with or without subsequent aromatics extraction to produce specified xylene isomers and particularly to produce para-xylene. In some instances, the feedstocks contain less than about 0.5, more preferably less than about 0.1, mass-% naphthenes.

Often the feedstocks will contain ethylbenzene, and in such instances, the ethylbenzene content is typically about 1 to about 60 mass-% of the total feedstock. In an aspect of this invention, an ethylbenzene containing feedstock is first subjected to catalytic dealkylation conditions to reduce the ethylbenzene content, and then subjected to the isomerization using the layered catalysts.

In the processes of this invention in which ethylbenzene is isomerized, typically the feed also contains naphthenes in an amount sufficient to enhance the ethylbenzene conversion. Naphthenes are cyclic paraffins and may include, for purposes herein, cyclic compounds having non-aromatic unsaturation in the ring structure. A convenient source of naphthenes is the isomerization process itself which produces naphthenes. Typically, the naphthenes that are recycled are monocyclic compounds, especially 5 and 6 carbon atom rings, having from 5 to 9 carbon atoms. The downstream unit operations will define the composition and amount of naphthenes being recycled. Generally, the naphthenes are present in an amount of about 2 to 20, preferably from about 4 to 15, mass-% of the feed. Equilibria may exist under isomerization conditions between naphthenes and aromatics. Thus, at isomerization conditions that convert a greater percentage of ethylbenzene, greater concentrations of naphthenes are preferred. As the naphthenes are a by-product of the isomerization, usually the isomerization unit is started up with the xylene and ethylbenzene feed and then the sought amount of naphthenes are permitted to build up for steady-state operation.

According to the process of the present invention, the feedstock, in the presence of hydrogen, is contacted with the layered catalyst described above. Contacting may be effected using the catalyst system in a fixed-bed system, a moving-bed system, a fluidized-bed system, and an ebullated-bed system or in a batch-type operation. In view of the danger of attrition loss of valuable catalysts and of the simpler operation, it is preferred to use a fixed-bed system. In this system, the feed mixture is preheated by suitable heating means to the desired reaction temperature, such as by heat exchange with another stream if necessary, and then passed into an isomerization zone containing catalyst. The isomerization zone may be one or more separate reactors with suitable means therebetween to ensure that the desired isomerization temperature is maintained at the entrance to each zone. The reactants may be contacted with the catalyst bed in upward-, downward-, or radial-flow fashion.

The isomerization is conducted under isomerization conditions including isomerization temperatures generally within the range of about 100° to about 550° C. or more, and preferably in the range from about 150° to 500° C. The pressure generally is from about 10 kPa to about 5 MPa absolute, preferably from about 100 kPa to about 3 MPa absolute. The isomerization conditions comprise the presence of hydrogen in a hydrogen to hydrocarbon mole ratio of between about 0.5:1 to 6:1, preferably about 1.1 or 2:1 to 5:1. A sufficient mass of catalyst comprising the catalyst (calculated based upon the content of molecular sieve in the catalyst composite) is contained in the isomerization zone to provide a weight hourly space velocity with respect to the liquid feed stream (those components that are normally liquid at STP) of from about 0.1 to 50 $hr^{-1}$, and preferably 0.5 to 25 $hr^{-1}$.

The isomerization conditions may be such that the isomerization is conducted in the liquid, vapor or at least partially vaporous phase. For convenience in hydrogen distribution, the isomerization is preferably conducted in at least partially in the vapor phase. When conducted at least partially in the vaporous phase, the partial pressure of $C_8$ aromatics in the reaction zone is preferably such that at least about 50 mass-% of the $C_8$ aromatics would be expected to be in the vapor phase. Often the isomerization is conducted with essentially all the $C_8$ aromatics being in the vapor phase.

The isomerization conditions are sufficient such that the xylene isomer content approaches equilibrium. The conditions are such that the isomerization product contains a xylene mixture is which para-xylene comprises at least about 23 mass-%, ortho-xylene at least about 21 mass-%, and meta-xylene at least about 48 mass-% based upon total xylenes. Often, the feedstock is para-xylene depleted, e.g., contains less than 5 mass-% para-xylene based upon total xylene content, and the mass ratio of para-xylene to total xylene in the product is at least about 0.235:1, and more preferably, at least about 0.237:1. While the isomerization conditions do not result in a xylene equilibrium being reached, the close approach of the isomerization to equilibrium typically results in an increase in the co-production of toluene and $C_9$ and higher aromatics. The thinness of the outer layer and the proximity of the hydrogenation metal component to the molecular sieve are believed to contribute to the ability to have only a low co-production of toluene and $C_9$ and higher aromatics. That is, the total toluene and trimethylbenzene make, based on the mass of the $C_8$ aromatics in the feedstock, is less than about 3, preferably less than about 2.5, and most preferably less than about 2, mass-%. Preferably the isomerization conditions result in little, if any, naphthenes being co-produced. Desirably the net naphthene make (based upon total $C_8$ aromatics in the feedstock) is less than about 0.5, preferably less than about 0.2, mass-%. Where very low net naphthene make is sought, molybdenum-containing catalysts are favored. Often, the net naphthene make using molybdenum catalysts can be less than about 0.05 mass-% based upon total $C_8$ aromatics in the feedstock.

In preferred catalysts, the binder comprises aluminum phosphate which is believed to further reduce the co-production of toluene and $C_9$ and higher aromatics.

The particular scheme employed to recover an isomerized product from the effluent of the reactors of the isomerization zone is not deemed to be critical to the instant invention, and any effective recovery scheme known in the art may be used. Typically, the isomerization product is fractionated to remove light by-products such as alkanes, naphthenes, benzene and toluene, and heavy by-products to obtain a $C_8$ isomer product. Heavy by-products include dimethylethylbenzene and trimethylbenzene. In some instances, certain product species such as ortho-xylene or dimethylethylbenzene may be recovered from the isomerized product by selective fractionation. The product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in U.S. Pat. Nos. 3,626,020, 3,696,107, 4,039, 599, 4,184,943, 4,381,419 and 4,402,832, incorporated herein by reference.

In the aspects of the processes of this invention where the feedstock for isomerization has been previously subjected to dealkylation conditions to reduce ethylbenzene content, the feedstock often contains from about 0.5 to 10 mass-% ethylbenzene based upon total $C_8$ aromatics. Thus there is little advantage in the layered catalyst exhibiting much activity toward dealkylation. For many catalysts, steaming the catalyst can reduce activity toward ethylbenzene dealkylation. Where dealkylation of ethylbenzene is desired to be accomplished during xylene isomerization, platinum group hydrogenation metal components are usually preferred. Generally, where ethylbenzene dealkylation is sought, the isomerization conditions are sufficient to convert at least about 50, preferably at least about 60, mass-% of the ethylbenzene in the feedstock.

Where the processes involve the isomerization of ethylbenzene, usually the isomerization conditions are sufficient that at least about 10, preferably between about 20 and 50, percent of the ethylbenzene in the feed stream is converted. Generally, the isomerization conditions do not result in a xylene equilibrium being reached. Often, the mole ratio of xylenes in the product stream is at least about 80, say, between about 85 and 95, percent of equilibrium under the conditions of the isomerization. Where the isomerization process is to generate para-xylene, e.g., from meta-xylene, the feed stream contains less than 5 mass-% para-xylene and the isomerization product comprises a para-xylene to xylenes mole ratio of between about 0.20:1 to 0.25:1.

EXAMPLES

The following examples are presented only to illustrate certain specific embodiments of the invention, and should not be construed to limit the scope of the invention as set forth in the claims. There are many possible other variations, as those of ordinary skill in the art will recognize, within the spirit of the invention.

Example I

Samples of catalyst are prepared.

Catalyst A: A molybdenum-impregnated aluminophosphate bound MFI catalyst is prepared to represent the catalyst of the invention. To a support material consisting of a 58 micron active layer of 50 mass-% MFI zeolite (38 Si/$Al_2$ ratio) and aluminophosphate on an inert alpha alumina core (0.11 centimeter diameter sphere) is added an aqueous solution of ammonium heptamolybdate to give 0.73 grams of molybdenum per 100 grams of MFI-aluminophosphate composition. After drying and calcination at 525° C. for 2 hours in air with 3 mol-% steam, the catalyst is reduced in hydrogen for 4 hours at 425° C.

Catalyst B: A platinum-impregnated aluminophosphate bound MFI catalyst is prepared. To a support material the same as used for Catalyst A is added an aqueous solution of tetra-ammine platinum chloride to give 0.034 grams of platinum per 100 grams of MFI-aluminophosphate composition. After drying and calcination at 525° C. for 2 hours in air with 3 mol-% steam, the catalyst is reduced in hydrogen for 4 hours at 425° C.

Catalyst C: A platinum-impregnated gamma alumina bound MFI catalyst is prepared. A support material consisting of a 38 micron active layer of 67 mass-% MFI zeolite (38 Si/$Al_2$ ratio) and gamma alumina binder on an inert alpha alumina core (0.11 centimeter diameter sphere) is treated with 10 mol-% steam in air at 525° C. for 3 hours. It is then contacted with an aqueous solution of tetra-ammine platinum chloride to give 0.042 grams of platinum per 100 grams of MFI-gamma alumina composition. After drying and calcination at 525° C. for 2 hours in air with 3 mol-% steam, the catalyst is reduced in hydrogen for 4 hours at 425° C.

Catalyst D: A molybdenum-impregnated gamma alumina bound MFI catalyst is prepared. To a support material consisting of a 60 micron active layer of 50 mass-% MFI zeolite (38 Si/$Al_2$ ratio) and gamma alumina binder on an inert alpha alumina core (0.11 centimeter diameter sphere) is added an aqueous solution of ammonium heptamolybdate to give 0.91 grams of molybdenum per 100 grams of MFI-gamma alumina composition. After drying and calcination at 525° C. for 2 hours in air with 3 mol-% steam, the catalyst is reduced in hydrogen for 4 hours at 425° C.

Catalyst E is the same support as is used to make Catalysts A and B.

Catalyst F is the support that is impregnated to make Catalyst C.

Example II

Catalysts A to F are evaluated in a pilot plant for the isomerization of a feed stream containing 15 mass-% ethylbenzene, 25 mass-% ortho-xylene and 60 mass-% meta-xylene. The pilot plant runs are at a hydrogen to hydrocarbon ratio of 4:1. The pilot plant runs are summarized in Table 1. The product data are taken at approximately 50 hours of operation. The weight hourly space velocities are based upon grams of zeolite loaded.

TABLE 1

| Catalyst | A | B | C Comp. | D Comp. | E Comp. | F Comp. |
|---|---|---|---|---|---|---|
| WHSV, $hr^{-1}$ | 15.9 | 15.9 | 43.6 | 31.8 | 31.5 | 43.6 |
| Inlet Temperature, ° C. | 400 | 370 | 382 | 378 | 372 | 392 | 360 |
| Pressure, kPa g | 689 | 689 | 689 | 689 | 689 | 689 | 689 |
| % Para-xylene/xylene | 23.9 | 23.9 | 23.8 | 23.7 | 23.9 | 23.2 | 23.5 |
| EB Conversion, % | 75 | 50 | 75 | 75 | 75 | 50 | 50 |
| Toluene and Trimethylbenzene yield, mass-% | 1.5 | 0.8 | 1.9 | 4.3 | 4.4 | 1.4 | 3.0 |

Example III

Catalyst G: To a support material consisting of a 200 micron active layer of 10 mass-% MTW zeolite (39:1 Si/$Al_2$ ratio) and gamma alumina on a gamma alumina core (0.16 centimeter diameter) is added an aqueous solution of chloroplatinic acid with 0.05 mass-% hydrochloric acid to provide a final platinum level of 0.32 mass-% on the catalyst. The impregnated pellets are then oxidized and chloride adjusted at 565° C. to yield 1.04 mass-% chloride on the catalyst, subjected to a reducing environment of hydrogen at 565° C., and sulfided with hydrogen sulfide to yield 0.09 mass-% sulfur on the catalyst. Scanning electron microscopy reveals that over 90 mass-% of the platinum is contained in the outer layer.

Catalyst H (comparative): To a support material consisting of a 200 micron active layer of 10 mass-% MTW zeolite (39:1 Si/Al$_2$ ratio) and gamma alumina on a gamma alumina core (0.16 centimeter diameter) is added an aqueous solution of chloroplatinic acid with 2 mass-% hydrochloric acid to provide a final platinum level of 0.31 mass-% on the catalyst. The impregnated pellets are then oxidized and chloride adjusted at 565° C. to yield 0.98 mass-% chloride on the catalyst, subjected to a reducing environment of hydrogen at 565° C., and sulfided with hydrogen sulfide to yield 0.09 mass-% sulfur on the catalyst. Scanning electron microscopy reveals that less than 75 percent of the platinum is contained in the outer layer.

Example IV

Catalysts G and H are evaluated in a pilot plant for conversion of a feed stream containing 15 mass-% ethylbenzene, 25 mass-% ortho-xylene and 60 mass-% meta-xylene. The pilot plant runs are at a hydrogen to hydrocarbon ratio of 4:1. The pilot plant runs are summarized in Table 2. The product data are taken at approximately 50 hours of operation. The weight hourly space velocities are based upon grams of zeolite loaded.

TABLE 2

| Catalyst | G | H |
| --- | --- | --- |
| WHSV, hr$^{-1}$ | 182 | 182 |
| Inlet Temperature, ° C. | 382 | 382 |
| Pressure, kPa g | 689 | 689 |
| % Para-xylene/xylene | 22.9 | 22.5 |
| EB conversion, % | 35 | 31 |
| Toluene and Trimethylbenzene yield, mass-% | 1.2 | 1.2 |

Example V

Catalyst I: A support material consisting of a 38 micron active layer of 67 mass-% MFI zeolite (38:1 Si/Al$_2$ ratio) and gamma alumina binder on an inert alpha alumina core (0.11 centimeter diameter) is treated with 40 vol-% steam in air at 650° C. for 6 hours. It is then contacted with an aqueous solution of perrhenic acid to give 0.36 grams Re per 100 grams of MFI-gamma alumina composition. After drying and calcination at 500° C. for 2 hours in air, the catalyst is reduced in hydrogen for 4 hours at 425° C. and sulfided with hydrogen sulfide to yield 0.03 mass-% sulfur on the catalyst.

Catalyst J: A support material consisting of a 60 micron active layer of 50 mass-% MFI zeolite (38:1 Si/Al$_2$ ratio) and gamma alumina binder on an inert alpha alumina core (0.11 centimeter diameter) is treated with 90 vol-% steam in air at 750° C. for 1.5 hours. It is then ion exchanged twice with excess ammonium nitrate solution at 60° C., washed, dried and calcined in air at 550° C. for 2 hours. It is then contacted with an aqueous solution of perrhenic acid to give 0.45 grams Re per 100 grams of MFI-gamma alumina composition. After drying and calcination at 500° C. for 2 hours in air, the catalyst is reduced in hydrogen for 4 hours at 425° C. and sulfided with hydrogen sulfide to yield 0.04 mass-% sulfur on the catalyst.

Example VI

Catalysts I and J are evaluated in a pilot plant for conversion of a feed stream containing 15 mass-% ethylbenzene, 25 mass-% ortho-xylene and 60 mass-% meta-xylene. The pilot plant runs are at a hydrogen to hydrocarbon ratio of 4:1. The pilot plant runs are summarized in Table 3. The product data are taken at approximately 50 hours of operation. The weight hourly space velocities are based upon grams of zeolite loaded.

TABLE 3

| Catalyst | I | J |
| --- | --- | --- |
| WHSV, hr$^{-1}$ | 16 | 16 |
| Inlet Temperature, ° C. | 392 | 402 |
| Pressure, kPa g | 689 | 689 |
| % Para-xylene/xylene | 23.7 | 23.7 |
| EB conversion, % | 16 | 19 |
| Toluene and Trimethylbenzene yield, mass-% | 0.3 | 0.6 |

Example VII

Catalyst K: Steamed and calcined aluminum-phosphate-bound MFI zeolite spheres are prepared using the method of Example I in U.S. Pat. No. 6,143,941. A catalyst is prepared by contacting the support with chloroplatinic acid and 5 mass-% nitric acid to give 210 mass-ppm platinum on the finished catalyst. After drying and calcining, the catalyst is reduced in hydrogen for 4 hours at 425° C.

Catalyst L: A support material consisting of a 60 micron active layer of 50 mass-% MFI zeolite (38:1 Si/Al$_2$ ratio) and gamma alumina binder on an inert alpha alumina core (0.11 centimeter diameter) is treated with 40 vol-% steam in air at 650° C. for 6 hours. It is then contacted with an aqueous solution of perrhenic acid to give 0.28 grams Re per 100 grams of MFI-gamma alumina composition. After drying and calcination at 500° C. for 2 hours in air, the catalyst is reduced in hydrogen for 4 hours at 425° C. and sulfided with hydrogen sulfide to yield 0.04 mass-% sulfur on the catalyst.

Catalyst M: A reactor loading was prepared consisting of 24 mass parts Catalyst K at the reactor inlet followed by 76 mass parts Catalyst L.

Catalysts K, L and M are evaluated in a pilot plant for conversion of a feed stream containing 15 mass-% ethylbenzene, 25 mass-% ortho-xylene and 60 mass-% meta-xylene. The pilot plant runs are at a hydrogen to hydrocarbon ratio of 4:1. The pilot plant runs are summarized in Table 4. The product data are taken at approximately 50 hours of operation. The weight hourly space velocities are based upon grams of zeolite loaded.

TABLE 4

| Catalyst | K | L | M |
| --- | --- | --- | --- |
| WHSV, hr$^{-1}$ | 10 | 22 | 6 |
| Inlet Temperature, ° C. | 383 | 382 | 382 |
| Pressure, kPa g | 689 | 689 | 689 |
| % Para-xylene/xylene | 20.4 | 21.6 | 23.9 |
| EB conversion, % | 79 | 7 | 78 |
| Toluene and Trimethylbenzene yield, mass-% | 1.2 | 0.1 | 1.3 |

What is claimed is:

1. A process for isomerizing xylene in a feedstock comprising a non-equilibrium mixture of one or more xylenes comprising contacting the feedstock with a catalytically-effective amount of layered catalyst under isomerization conditions sufficient to provide a xylene-containing isomerization product stream in which of the xylenes, para-xylene comprises at least about 23 mass-%, ortho-xylene at least about 21 mass-%, and meta-xylene at least about 48 mass-%, said catalyst comprising a core having a major dimension of at least about 300 microns, a layer on said core, said layer comprising molecular sieve having a pore diameter of from about 4 to 8 angstroms and a binder and having a thickness less than about 250 microns, and at least one hydrogenation metal component selected from metals of Groups 6 to 10 of the Periodic Table (IUPAC), wherein at least about 75 mass-% of the hydrogenation metal component in the catalyst is contained in the layer, wherein the net production of toluene and trimethylbenzene is less than about 3 mass-% of the total xylenes and ethylbenzene, if present, in the feedstock.

2. The process of claim 1 wherein the feedstock contains less than about 5 mass-% para-xylene based on total xylenes and the isomerization product stream contains at least about 23.5 mass-% para-xylene based on total xylenes in the product stream.

3. The process of claim 2 wherein the binder comprises aluminum phosphate.

4. The process of claim 2 wherein the molecular sieve comprises at least one of MFI, MEL, MTT, UZM-8 and MTW molecular sieves.

5. The process of claim 4 wherein the layer has a thickness between about 20 and 200 microns.

6. The process of claim 5 wherein the hydrogenation metal component comprises at least one of molybdenum, rhenium, ruthenium, rhodium, palladium, iridium, and platinum.

7. The process of claim 1 wherein the core comprises alumina.

8. The process of claim 7 wherein the core comprises alpha-alumina.

9. The process of claim 1 wherein the core has a spherical structure.

10. The process of claim 1 wherein the core has a monolithic structure.

11. The process of claim 1 wherein the feedstock comprises ethylbenzene.

12. The process of claim 11 wherein the isomerization conditions include ethylbenzene dealkylation conditions and the feedstock contains less than 0.5 mass-% naphthenes.

13. The process of claim 12 wherein at least about 50 mass-% of the ethylbenzene is converted.

14. The process of claim 12 wherein the hydrogenation metal component comprises molybdenum.

15. The process of claim 12 wherein the binder comprises aluminum phosphate.

16. The process of claim 12 wherein the hydrogenation metal component is platinum.

17. The process of claim 11 wherein the feedstock comprises naphthenes and the isomerization conditions include ethylbenzene isomerization conditions.

18. The process of claim 1 wherein the feedstock has been subjected to dealkylation prior to isomerization.

19. The process of claim 18 wherein the net production of naphthenes is less than about 0.02 mass-% of the total xylenes and ethylbenzene in the feedstock.

20. The process of claim 18 wherein the hydrogenation metal component comprises rhenium.

* * * * *